United States Patent [19]

Lai

[11] Patent Number: 5,010,179

[45] Date of Patent: Apr. 23, 1991

[54] PROCESS FOR THE PREPARATION OF MIXED, SYMMETRICAL AZONITRILE DICARBOXYLIC DICYANO ACIDS AND INITIATORS

[75] Inventor: John T. Lai, Broadview Heights, Ohio

[73] Assignee: The B. F. Goodrich Company, Akron, Ohio

[21] Appl. No.: 457,058

[22] Filed: Dec. 26, 1989

[51] Int. Cl.$^5$ .................. C07C 245/04; C08F 4/04
[52] U.S. Cl. .................. 534/586; 526/219; 534/583; 534/587; 534/838; 534/886; 534/887
[58] Field of Search ............... 534/838, 886, 887, 586, 534/587, 583; 526/218, 219

[56] References Cited

U.S. PATENT DOCUMENTS 3,541,132  11/1970  Knowles ..................... 534/586 X
4,252,717   2/1981  Wake et al. ................. 534/838 X Primary Examiner—Floyd D. Higel
Attorney, Agent, or Firm—Daniel J. Hudak

[57] ABSTRACT

The preparation of mixed, symmetrical azonitrile initiators prepared from keto acids and aminonitrile is disclosed. A keto acid of the formula

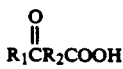

is reacted with $M(CN)_x$ and an ammonia source to obtain an aminonitrile metal carboxylate of the formula

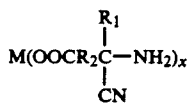

The aminonitrile metal carboxylate is reacted with $M_1(OCl)_x$ in the presence of a surfactant to form an azonitrile metal carboxylate. The excess $M_1(OCl)_x$ is reacted with an aminonitrile of the formula

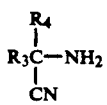

in the presence of the surfactant to form a symmetrical azonitrile initiator

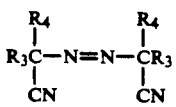

The aminonitrile metal carboxylate is reacted with mineral acid to give the symmetrical azonitrile compound of the formula

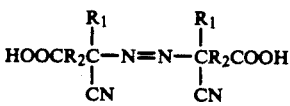

$R_1$ is an alkyl group containing from about 1 to about 12 carbon atoms and $R_2$ is an alkylene group containing from 1 to about 12 carbon atoms. M is a metal comprising lithium, sodium, potassium, magnesium or calcium; $M_1$ is a metal comprising sodium, potassium or calcium; and X is the valence of M and $M_1$.

23 Claims, No Drawings

PROCESS FOR THE PREPARATION OF MIXED, SYMMETRICAL AZONITRILE DICARBOXYLIC DICYANO ACIDS AND INITIATORS

FIELD OF THE INVENTION

The present invention relates to an improved process for the preparation of mixed, symmetrical azonitrile initiators. There is a two-fold purpose for making mixed, symmetrical azonitrile initiators: (1) simple ketones such as acetone are less expensive than keto acids such as levulinic acid and (2) some applications do not need high viscosity; that is, a non-carboxylic acid azonitrile initiator is less viscous than a carboxylic acid azonitrile initiator.

BACKGROUND

It is known in the art to prepare diazocyano acids using a keto acid or a sodium salt of a keto acid as the starting material.

U.S. Pat. No. 4,028,345 (Moore, Jr., June 7, 1977) relates to a process comprising reacting an alphaaminonitrile selected from

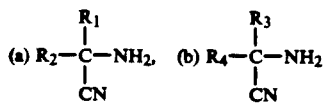

and mixtures thereof wherein $R_1$, $R_2$, $R_3$, and $R_4$ are selected from (1) hydrocarbyl radicals of 1 to 8 carbon atoms, (2) hydrocarbyl radicals of 1 to 8 carbon atoms substituted with carboxyl, hydroxyl or -OR wherein R is selected from a hydrocarbyl radical of 1 to 4 carbon atoms, (3) cyclohydrocarbyl radicals of 3 to 6 carbon atoms and (4) cyclohydrocarbyl radicals of 3 to 11 carbon atoms formed by combining $R_1$ and $R_2$ or $R_3$ and $R_4$ with 5 to 15 percent by weight based on the reaction mixture of a metal hypochlorite, $M(OCl)_x$, where M is selected from sodium, potassium or calcium and x is the valence of M, in an aqueous medium in the presence of 0.25 to 10 percent by weight, based on the weight of aminonitrile, of a surface active compound or mixtures thereof having an HLB of 8 to 35 at a temperature of $-10°$ C. to $30°$ C., said hypochlorite and alpha-aminonitrile being present in an equivalent ratio of 1:1 to 2:1 of hypochlorite to aminonitrile and recovering from the reaction mixture an aliphatic azonitrile of the formula

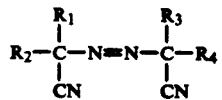

U.S. Pat. Nos. 4,684,717 and 4,684,718 (Ashitaka et al, Aug. 4, 1987) provide a process for the preparation of diazocyano acid, which comprises reacting a keto acid or its sodium salt with a cyanogen compound such as sodium cyanide or hydrogen cyanide and a hydrazine in water to form a concentrated aqueous solution of a hydrazo compound, adding acetone and/or water to the concentrated aqueous solution to form a solution of the hydrazo compound, adding chlorine gas to the solution to oxidize the hydrazo compound and form a diazocyano acid, and separating the diazocyano acid from the obtained reaction mixture.

U.S. Pat. No. 4,831,096 (MacLeay, May 16, 1989) relates to mixtures of azoalkanes of varying thermal stabilities, at least one of which is an unsymmetrical azoalkane (R-N=N-R'). These unsymmetrical azoalkanes are prepared by reacting four equivalents of a mixture of two or more primary alkyl, cycloalkyl or aralkyl amines with one equivalent of sulfuryl chloride in an inert solvent and oxidizing the resulting mixture of sulfamide products with basic bleach. The unsymmetrical azoalkanes can be separate from the symmetrical azoalkanes by a variety of conventional techniques. The azoalkane mixtures are polymerization initiators for vinyl monomers and curing agents for unsaturated polyester resins.

SUMMARY OF THE INVENTION

This invention relates to a process for preparing mixed, symmetrical azonitrile initiators of the formulae:

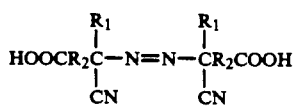

and

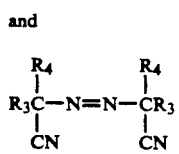

In the above formulae, $R_1$ is an alkyl group containing from 1 to about 12 carbon atoms, $R_2$ is a direct bond or an alkylene group containing from 1 to about 12 carbon atoms. $R_2$ may also be a cycloalkylene or alkyl cycloalkylene group containing from 3 to about 12 carbon atoms. $R_3$ and $R_4$ are alkyl groups containing from 1 to about 12 carbon atoms. One of $R_3$ and $R_4$ may be an alkoxy group of from 1 to about 4 carbon atoms.

DETAILED DESCRIPTION OF THE INVENTION

Within U.S. Pat. No. 4,028,345, the coupling of aminonitriles requires as little as 0.25 percent by weight of a surfactant based on the aminonitrile. It is surprising that in making mixed, symmetrical azonitrile initiators from an aminonitrile and an aminonitrile metal carboxylate, as little as 0.05 percent active up to about 0.20 percent active of a surfactant based on the total weight of aminonitrile metal carboxylate and aminonitrile can be used.

Mixed, symmetrical azonitrile initiators prepared by the process of this invention are: less expensive due to the utilization of acetone or other lower alkyl ketones and have a lower viscosity since the mixed, symmetrical azonitrile initiator has terminal end groups of either carboxyl or alkyl.

The various important properties of mixed, symmetrical azonitrile initiators are physical state, solubility, volatility, toxicity, thermal stability and initiator efficiency and these properties are dependent upon the nature of the end groups carboxyl and alkyl. The thermal stability of mixed, symmetrical azonitrile initiators is intermediate between the stabilities of symmetrical azonitrile initiators HOOCR-N=N-RCOOH or R-N=N-R and the unsymmetrical azonitrile initiator HOOC-N=N-R. Many of the mixed, symmetrical azonitrile initiators have unique thermal and initiator properties which cannot be duplicated by the purely symmetrical or purely unsymmetrical azonitrile initiators. Mixtures of symmetrical azonitrile initiators have unique thermal and initiator properties that may extend over a wide temperature range depending upon the end groups.

It is known in the art that a symmetrical azonitrile initiator of the formula R-N=N-R made from an aminonitrile utilizing about 0.25 percent of a surfactant is obtained in a low yield. Mixed, symmetrical azonitrile initiators of the formula HOOCR-N=N-RCOOH and R-N=N-R made from an aminonitrile metal carboxylate and aminonitrile utilizing about 0.20 percent surfactant is obtained in a high yield.

The following reactants are utilized in the preparation of mixed, symmetrical azonitrile initiators: keto acid, metal cyanide, ammonia source, metal hypochloride, amino nitrile, surfactant, reducing agent and neutralization agent.

THE KETO ACID

The keto acids having utility in this invention are of the general formula

R₁CR₂COOH $R_1$ is an alkyl group containing from 1 to about 12 carbon atoms, preferably from 1 to about 6 carbon atoms and most preferably from 1 to about 3 carbon atoms. Such groups are known to those skilled in the art. Examples include methyl, ethyl, propyl, isopropyl, butyl, isobutyl and t-butyl.

$R_2$ is an alkylene or cycloalkylene group containing from 1 to about 12 carbon atoms and preferably 1 to about 6 carbon atoms. When $R_2$ is not cyclic $R_2$ it most preferably contains from 1 to about 4 carbon atoms. When $R_2$ is cyclic it most preferably contains from about 3 to about 6 carbon atoms. Some examples of $R_2$ cyclic alkylenes are

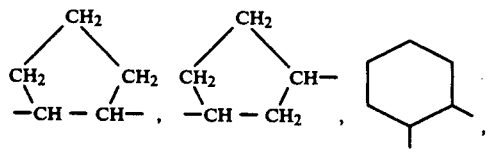

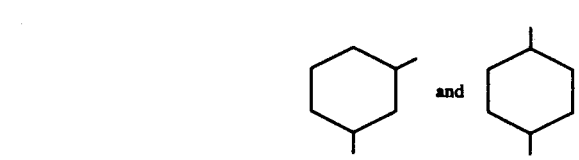

When $R_2$ is not cyclic, examples are methylene, ethylene, propylene, butylene, as well as any branching thereof. The following table lists a few of the many keto acids having utility in this invention. This list is merely illustrative and is not meant to be all-inclusive. A preferred keto acid is levulinic acid.

TABLE I

| | Keto Acids | |
|---|---|---|
| R₁ | R₂ | Name |
| CH₃ | non-existent | pyruvic acid |
| CH₃ | CH₂ | 3-oxobutanoic acid |

TABLE I-continued

| | Keto Acids | |
|---|---|---|
| R₁ | R₂ | Name |
| CH₃ | CH₂CH₂ | levulinic acid |
| CH₃ | CH₂CH₂CH₂ | 5-oxohexanoic acid |
| CH₃ | CH₂CH₂CH₂CH₂ | 6-oxoheptanoic acid |
| CH₃ | CH₂CH₂CH₂CH₂CH₂ | 7-oxooctanoic acid |
| CH₃CH₂ | non-existent | 2-oxobutanoic acid |
| CH₃CH₂ | CH₂ | 3-oxopentanoic acid |
| CH₃CH₂ | CH₂CH₂ | 4-oxohexanoic acid |
| CH₃CH₂ | CH₂CH₂CH₂ | 5-oxoheptanoic acid |
| CH₃CH₂CH₂ | CH₂CH₂ | 4-oxoheptanoic acid |
| CH₃ | CH₂CH | 2-methyllevulinic acid |
| | CH₃ | |

THE METAL CYANIDE

One mole of the keto acid is reacted with from about 1 to about 2, preferably 1 to about 1.5, and most preferably from about 1 to about 1.1 equivalents of a metal cyanide of the formula M(CN)$_x$ wherein the metal M comprises lithium, sodium, potassium, magnesium, or calcium and x is the valence of M. An equivalent of M(CN)$_x$ is its weight in grams, pounds, etc. divided by its equivalent weight. The equivalent weight of M(CN)$_x$ is equal to its molecular weight divided by the valence of x. An equivalent weight of NaCN is 49 (49 molecular weight divided by valence of 1) and 49 grams is one gram-equivalent of NaCN. An equivalent weight of Ca(CN)₂ is 46 (92 molecular weight divided by valence of 2) and 46 grams is one gram-equivalent of Ca(CN)₂. The reaction of the keto acid with M(CN)$_x$ is a reversible addition reaction that strongly favors the right side with very little by-products formed. A preferred metal cyanide is sodium cyanide.

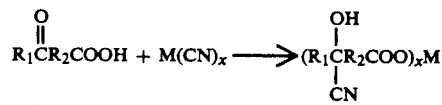

In order to convert the cyanohydrin metal carboxylate to an aminonitrile metal carboxylate, 1 to about 2 moles of an ammonia source per 0.5-1 moles of keto acid is introduced.

AMMONIA SOURCE

As examples of the ammonia source, there can be mentioned both gaseous ammonia and concentrated ammonium hydroxide (28-30%).

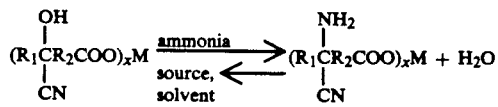

When the ammonia source is concentrated ammonium hydroxide, water is used as a solvent; when the ammonia source is ammonia gas, a lower carbon alcohol is used.

AMINONITRILE

Aminonitriles having utility in this invention are of the general formula

$R_3$ and $R_4$ are alkyl groups independently containing from 1 to about 12 carbon atoms, preferably from 1 to about 6 carbon atoms and most preferably from 1 to about 4 carbon atoms. The alkyl groups may be branched or straight chained. One of the groups $R_3$ or $R_4$ may also be an alkoxy group containing from 1 to about 4 carbon atoms. Preferred aminonitriles are acetone aminonitrile wherein $R_3$ and $R_4$ are methyl groups and 2-butanone aminonitrile wherein $R_3$ is methyl and $R_4$ is an ethyl group.

THE METAL HYPOCHLORITE

The aminonitrile metal carboxylate and aminonitrile are converted to the azonitrile metal carboxylate and azonitrile respectively by action of aqueous $M_1(OCl)_x$. $M_1$ comprises sodium, potassium, or calcium and x is the valence of the metal M. Sodium is the preferred metal. The concentration of $M_1(OCl)_x$ in water is from about 2 to about 20 percent, preferably from about 5 to about 17 percent, and most preferably from about 9 to about 16 percent.

After the aminonitrile metal carboxylate is formed, coupling within the aminonitrile metal carboxylate is effected by the metal hypochlorite. An aminonitrile is added and the remaining $M_1(OCl)_x$ causes coupling within the aminonitrile. This coupling takes place in the presence of a surfactant.

THE SURFACTANT

The surfactant compounds of the present invention are defined as any compound or mixture of compounds that affects the surface tension when mixed with water and is not adversely affected in its properties if it reacts with the hypochlorite, aminonitrile metal carboxylate, aminonitrile or final product of the present invention.

The inclusion of a surfactant in the process of coupling an aminonitrile metal carboxylate to another aminonitrile metal carboxylate or an aminonitrile to another aminonitrile to give mixed, symmetrical azonitrile initiators with a metal hypochlorite enables the reaction to proceed in an aqueous medium.

Surfactants useful in the process of the present invention may be a single surfactant or mixtures thereof. Cationic surfactants are preferred.

Cationic surfactants include various types of nitrogen containing compounds such as fatty alkyl amines and their salts and quaternary ammonium compounds or more specifically tetraalkyl ammonium compounds. Tetraalkyl ammonium halides are considered to be the most important type of cationic surfactants. The tetraalkyl ammonium chlorides or bromides are preferred. The tetraalkyl ammonium chlorides are considered the most preferred cationic surfactant. What is meant by tetraalkyl ammonium in the compounds described herein is that they contain a nitrogen atom to which four separate carbon atoms are attached.

Representative examples of tetraalkyl ammonium surfactants of the present invention include:

| Compound | Trade Name | Manufacture |
|---|---|---|
| Disoya dimethyl ammonium chloride | Arquad 25-75[1] | Armak Co. |
| Ditallow Imidazolinium quaternary salt | Alkaquat T | Alkaril Chem. |
| Cetyl trimethyl ammonium bromide | Retarder LAN | DuPont Co. |
| Quaternized polyoxyethylene cocoamine | Ethoquad C/25[2] | Armak Co. |
| Tallow trimethyl ammonium chloride | Arquad T-50[3] | Armak Co. |
| Tetradecyl trimethyl ammonium chloride | | Armak Co. |
| Dodecyl trimethyl ammonium chloride | Arquad 12-50[3] | Armak Co. |
| Hexadecyl trimethyl ammonium chloride | Arquad 16-50[3] | Armak Co. |
| Octadecyl trimethyl ammonium chloride | Arquad 15-50[3] | Armak Co. |

[1] 75 percent aqueous solution
[2] 25 percent aqueous solution
[3] 50 percent aqueous solution A preferred cationic surfactant is Arquad 16-50.

Within the process of the present invention, the surfactant is present in a catalytic amount of from about 0.05 percent active to no more than about 0.20 percent active, preferably from about 0.08 percent active up to about 0.20 percent active and most preferably from about 0.12 percent active up to about 0.20 percent active by weight based on the total weight of aminonitrile metal carboxylate and aminonitrile. By active surfactant, it is meant the weight of the surfactant less any diluent according to the below equations:

weight active surfactant = (weight of surfactant)(100% − % diluent).

If a surfactant is 75 percent aqueous and 0.1 g is employed, then:

weight active surfactant = (0.1 g)(100% − 75%) = 0.0025 g.

REDUCING AGENT

After the azonitrile metal carboxylate and azonitrile are formed, the excess unreacted $M_1(OCl)_x$ is removed for environmental concerns. This is done by utilizing a reducing agent such as sodium bisulfite or sodium sulfite. The reducing agent is added as a 20 percent by weight aqueous solution. Just enough reducing agent is added to provide a negative test for KI-starch test paper; i.e., KI-starch paper is no longer darkened by $I_2$.

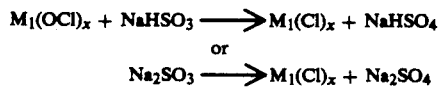

NEUTRALIZATION AGENT

Once the metal hypochlorite is reduced, the azonitrile metal carboxylate is ready to be neutralized to form the azonitrile acid (I) within the mixed, symmetrical azonitrile initiator. The neutralization agent is usually an inorganic acid such as hydrochloric acid, nitric acid or sulfuric acid. The preferred mineral acid is hydrochloric acid. The azonitrile metal carboxylate is of the following structure

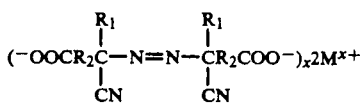

where M is lithium, sodium, potassium, magnesium, or calcium and x is the valence of M. Acidifying the above azonitrile metal carboxylate yields the azonitrile initiator of the structure:

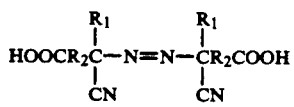

The composition prepared by the process of the present invention are formed by preparing a mixture of metal cyanide, ammonia source and solvent. To this mixture is added a keto acid to form the aminonitrile metal carboxylate,

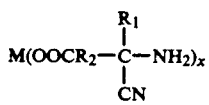

The order of addition can be varied. It may be carried out as above or the metal cyanide can be suspended or dissolved in solvent, the keto acid added to generate a cyanohydrin followed by the addition of the ammonia source.

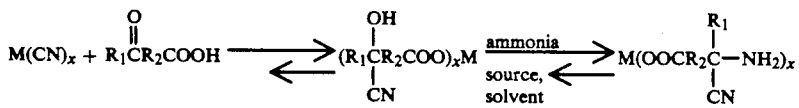

Or the ammonium salt of the acid can be formed first followed by the addition of metal cyanide.

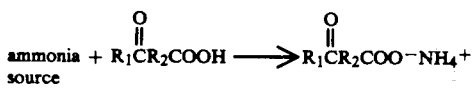

then

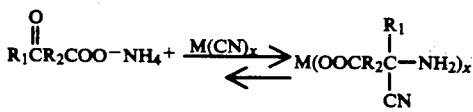

The preferred method is to mix metal cyanide and ammonium hydroxide in water followed by additions of the keto acid. The advantages are (a) the pH is always greater than 8, therefore no danger of HCN escaping and (b) all intermediates remain in solutions—no solidification can occur.

If excess ammonia is present after the formation of the aminonitrile metal carboxylate, the overall yield of the azonitrile initiator (I) is not diminished but rather more metal hypochlorite will have to be used to convert the aminonitrile metal carboxylate to the azonitrile metal carboxylate. Excess ammonia is removed by passing an inert gas such as nitrogen or argon through the reaction medium. The solvent can be water or a lower carbon alcohol such as methanol or ethanol, preferably methanol. If a lower carbon alcohol is used as the solvent, it has to be removed and when this is done, the aminonitrile metal carboxylate is obtained as an oil which tends to solidify. If the lower carbon alcohol is not removed before the addition of the metal hypochlorite, lower yields of azonitrile initiators are obtained. An advantage of utilizing water as the solvent is that the processing is easier due to the fact that the aminonitrile metal carboxylate does not have to be isolated.

The molar ratio of keto acid: ammonia source is from about 0.5–1:1–2, preferably from 1:1–1.5 and most preferably 1:1–1.1. After reaction of the ammonia source, nitrogen is bubbled through the reaction mixture to remove excess ammonia source.

Once the aminonitrile metal carboxylate solution is formed, $M_1(OCl)_x$ and a surfactant are added followed by the dropwise addition of an aminonitrile such as acetone aminonitrile. Alternatively, the $M_1(OCl)_x$ and surfactant can be added to the aminonitrile and the aminonitrile metal carboxylate can be added dropwise to the aminonitrile solution. The molar ratio of aminonitrile metal carboxylate:aminonitrile is from about 0.5–10:1, preferably from about 0.5–5:1 and most preferably from about 0.9–1.1:1.

The equivalent weight ratio of the sum of the aminonitrile metal carboxylate and aminonitrile: $M_1(OCl)_x$ is from about 1:1.0–2.75 preferably 1:1.1–2.0 and most preferably 1:1.2–1.5. The excess $M_1(OCl)_x$ is neutralized with up to about a 100 percent excess of $NaHSO_3$ or $Na_2SO_3$, preferably a 0–10 percent excess and most preferably a 0–2 percent excess of reducing agent. The reaction temperature for any of the intermediates is from about 0° C. to about 60° C. preferably from about 25° to about 50° C. and most preferably from about 30° to about 40° C. The reaction temperature for the coupling of aminonitrile metal carboxylate and aminonitrile to form the mixed symmetrical azonitrile initiators is from about −15° to about 35° C., preferably from about 0° to about 25° C. and most preferably from about 0° to about 10° C.

The mixed, symmetrical azonitriles produced by the process of this invention can be used as a polymerization initiator in emulsion dispersion and solution polymerization systems. Polymerization involving vinyl chloride, methyl methacrylate, and butadiene-styrene are merely examples of such systems in industry that would benefit from the use of such initiators.

If a mixed, symmetrical azonitrile initiator containing a low salt content is desired, the azonitrile initiator can be washed with water either before or after isolation.

The following examples are illustrative of the preparation of azonitrile initiators. Unless otherwise indicated, all parts and percentages are by weight.

EXAMPLE 1

Charged to a 50 milliliter, three-neck round bottom flask fitted with a thermometer and magnetic stirrer was 5.15 parts (0.105 moles) sodium cyanide, 4 parts water and 7.0 parts (0:115 moles) 28 percent ammonium hydroxide in water. The contents were stirred and cooled in an ice water bath. At between 0°–5° C. 11.6 parts (0.1 mole) levulinic acid dissolved in 7 parts water was added drop-wise. After completion of the levulinic acid addition, the water bath was removed and the temperature was raised to 35° C. Nitrogen was bubbled through the solution to remove excess ammonia.

To a 300 milliliter jacketed flask with a thermometer and mechanical stirrer was added 128.4 parts of a 14 percent aqueous solution of sodium hypochlorite and 0.1 part of Arquad 16/50 surfactant. The vial containing the surfactant was rinsed with 1 part water, added to the reaction vessel, and the temperature was lowered to 0° C. The contents of the 50 milliliter flask were added dropwise over two hours at a temperature range of between 0° C. to 5° C. To the contents were added 7.8 parts of a 20 percent aqueous solution of sodium sulfite to reduce the excess sodium hypochlorite. The pH was about 12 and there was no reaction with KI paper. About 15 parts concentrated hydrochloric acid were added to convert the sodium salt to the free carboxylic acid. The pH was about 1. The contents were filtered and the solid product water-washed to obtain 17.7 parts of a white solid that is a mixture of the following structures:

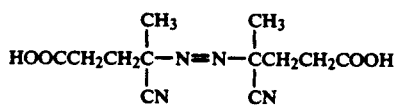

and

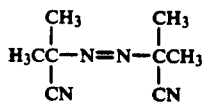

An HNMR in MeOD showed that the white solid is approximately a 1:1 by weight mixture of the above structures.

EXAMPLE 2

The aminonitrile of sodium levulinate in water solution was prepared in the same manner and in the same amount as in Example 1.

To a 300 milliliter jacketed flask with a thermometer and mechanical stirrer was added 128.4 parts of a 14 percent aqueous solution of sodium hypochlorite and 0.1 part of Arquad 16/50 surfactant. The vial containing the surfactant was rinsed with 1 part water, added to the reaction vessel, and the temperature was lowered to 0° C. and 9.8 parts (0.1 mole) 2-amino-2-methylbutyonitrile was added dropwise at a temperature of between 0° to 5° C. The aminonitrile addition took 30 minutes. The contents were permitted to stir for 5 minutes after completion of the addition. The aminonitrile of sodium levulinate solution was added dropwise over 45 minutes at a temperature range of between 0° and 5° C. about 15 minutes. After the addition was complete, 50 parts of a 20 percent aqueous solution of sodium sulfite were added to reduce the excess sodium hypochlorite. Concentrated hydrochloric acid was added to convert the sodium salt to the free carboxylic acid. The pH was between 1 and 2. The contents were filtered and the solid product water-washed to obtain 18.6 parts of a white solid having the following structure:

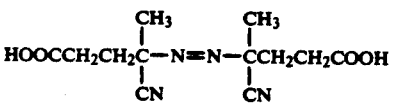

and

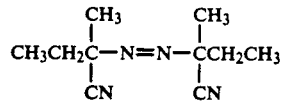

While in accordance with the Patent Statutes, the best mode and preferred embodiment has been set forth, the scope of the invention is not limited thereto, but rather by the scope of the attached claims.

What is claimed is:

1. A process for the preparation of mixed, symmetrical azonitrile initiators, comprising; forming

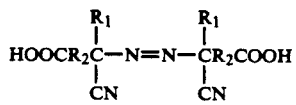   I and

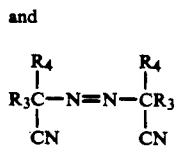   II by reacting a keto acid of the formula

wherein $R_1$ is an alkyl containing from 1 to 12 carbon atoms and $R_2$ is a direct bond, or an alkylene containing from 1 to 12 carbon atoms or a cycloalkylene containing from about 3 to about 12 carbon atoms, with from 1 to 2 equivalents of $M(CN)_x$ per mole of keto acid wherein M is a metal selected from the group consisting of lithium, sodium, potassium, magnesium, or calcium and x is the valence of M and an ammonia source in a molar ratio of keto acid: ammonia source of from about 1:1–4 in the presence of a solvent to form an aminonitrile metal carboxylate of the formula

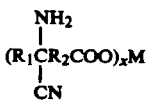

removing excess ammonia source, removing methanol if used as a solvent, reacting said aminonitrile metal carboxylate with $M_1(OCl)_x$ in the presence of a surfactant wherein $M_1$ is a metal selected from the group consisting of sodium, potassium, or calcium and x is the valence of M to form an azonitrile metal carboxylate comprising

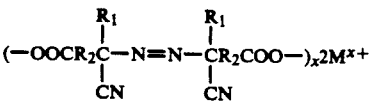   III and also
reacting an aminonitrile of the formula

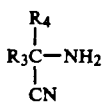

in the presence of a surfactant and $M_1(OCl)_x$ to form a symmetrical azonitrile initiator

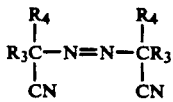  II wherein $R_3$ and $R_4$ are alkyl independently containing from 1 to about 12 carbon atoms or one of $R_3$ and $R_4$ is an alkoxy of from 1 to about 4 carbon atoms wherein the molar ratio of aminonitrile metal carboxylate:aminonitrile is from about 0.5–10:1, wherein the surfactant is from about 0.05 percent active to about 0.20 percent active by weight based on the total weight of aminonitrile metal carboxylate and aminonitrile, and wherein the equivalent weight ratio of the sum of the aminonitrile metal carboxylate and aminonitrile: $M_1(OCl)_x$ is from about 1:1.0–2.75, and reducing excess $M_1(OCl)_x$ with a reducing agent and further neutralizing the metal azonitrile carboxylate to form

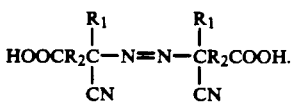  I

2. The process of claim 1 wherein the symmetrical azonitrile initiator

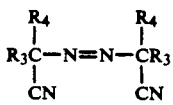  II is formed subsequent to the formation of the azonitrile metal carboxylate

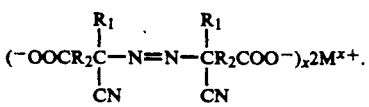  III

3. The process of claim 1 wherein the azonitrile metal carboxylate

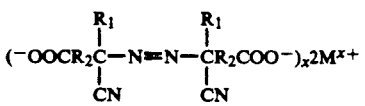  III is formed subsequent to the formation of the symmetrical azonitrile initiator

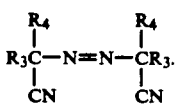  II

4. The process of claim 1, wherein the symmetrical azonitrile initiator

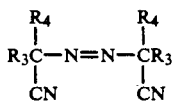  II is formed subsequent to the formation of the azonitrile metal carboxylate

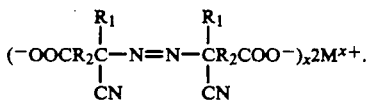  III

5. A process for the preparation of mixed, symmetrical azo compounds, comprising:

reacting a keto acid

wherein $R_1$ is an alkyl containing from 1 to 12 carbon atoms and $R_2$ is a direct bond, or an alkylene containing from 1 to about 12 carbon atoms with from 1 to about 2 equivalents of $M(CN)_x$ per mole of keto acid, wherein M is a metal selected from the group consisting of lithium, sodium, potassium, magnesium, or calcium and x is the valence of M to form a cyanohydrin metal carboxylate of the formula

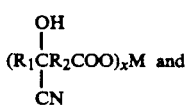 and reacting said cyanohydrin metal carboxylate with an ammonia source in a molar ratio of keto acid:ammonia source of from about 1:1–4 in the presence of water as a solvent to form an aminonitrile metal carboxylate of the formula

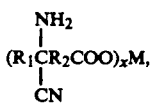

removing excess ammonia source and reacting said aminonitrile metal carboxylate with $M_1(OCl)_x$ in the presence of a surfactant wherein $M_1$ is a metal selected from the group consisting of sodium, potassium, or calcium and x is the valence of $M_1$ to form an azonitrile metal carboxylate comprising

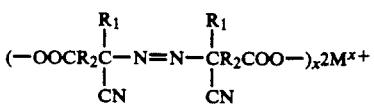  III and also
reacting an aminonitrile of the formula

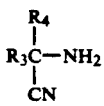

in the presence of a surfactant and $M_1(OCl)_x$ and x is the valence of $M_1$ to form a symmetrical azonitrile initiator

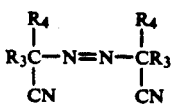
          II wherein $R_3$ and $R_4$ are alkyl independently containing from 1 to about 12 carbon atoms or one of $R_3$ and $R_4$ is an alkoxy of from 1 to about 4 carbon atoms wherein the molar ratio of aminonitrile metal carboxylate:aminonitrile is from about 0.5–10:1, wherein the surfactant is from about 0.05 percent active to about 0.20 percent active by weight based on the total weight of aminonitrile metal carboxylate and aminonitrile, and wherein the equivalent weight ratio of the sum of the aminonitrile metal carboxylate and aminonitrile: $M_1(OCl)_x$ is from about 1:1.0–2.75, and reducing excess $M_1(OCl)_x$ with a reducing agent and further neutralizing the azonitrile metal carboxylate to form

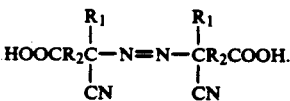
          I

6. The process of claim 5, wherein the symmetrical azonitrile initiator

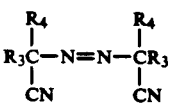
          II is formed subsequent to the formation of the azonitrile metal carboxylate

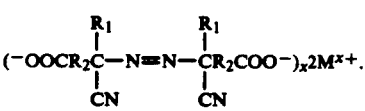
          III

7. The process of claim 5 wherein the azonitrile metal carboxylate

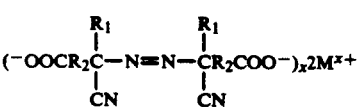
          III is formed subsequent to the formation of the symmetrical azonitrile initiator

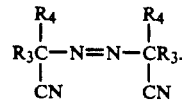
          II

8. The process of claim 5, wherein the symmetrical azonitrile initiator

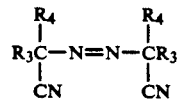
          II is formed subsequent to the formation of the azonitrile metal carboxylate

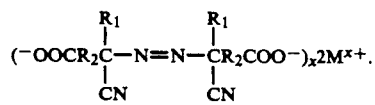
          III

9. The process of claim 5 wherein the azonitrile metal carboxylate

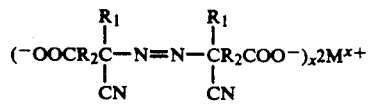
          III is formed subsequent to the formation of the symmetrical azonitrile initiator

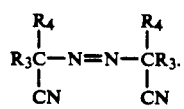
          II

10. The process of claim 1, wherein $R_1$ is an alkyl containing from 1 to about 6 carbon atoms, and $R_2$ is an alkaline containing from 1 to about 6 carbon atoms, or a cycloalkaline containing from about 3 to about 6 carbon atoms.

11. The process of claim 10, wherein the molar ratio of said keto acid to said ammonia source is 1:1–1.5, and wherein the molar ratio of said metal cyanide to said keto acid is 1–1.5:1.

12. The process of claim 11, wherein said surfactant is cationic and said surfactant is from about 0.08 percent to about 0.20 percent active.

13. The process of claim 12, wherein $R_3$ and $R_4$ are methyl, or $R_3$ is methyl, and $R_4$ is ethyl, and said aminonitrile metal carboxylate:aminonitrile ratio is from about 0.5–5:1, and said equivalent weight ratio of the sum of aminonitrile metal carboxylate and aminonitrile: $M_1(OCl)_x$ is from about 1:1.1–2.0, wherein said ammonia source is gaseous ammonia or concentrated ammonium hydroxide, and wherein said solvent is water or methanol.

14. The process of claim 13, wherein said reducing agent is sodium bisulfite or sodium sulfite.

15. The process of claim 14, wherein M is sodium.

16. The process of claim 15, wherein the azonitrile metal carboxylate is neutralized with a mineral acid comprising nitric acid, sulfuric acid, or hydrochloric acid.

17. The process of claim 5, wherein $R_1$ is an alkyl containing from 1 to about 3 carbon atoms, and $R_2$ is an alkaline containing from 1 to about 3 carbon atoms or a cycloalkaline containing from about 3 to about 6 carbon atoms.

18. The process of claim 17, wherein the molar ratio of said keto acid to said ammonia source is 1:1–1.2, and wherein the molar ratio of said metal cyanide to said keto acid is 1–1.1:1.

19. The process of claim 18, wherein said surfactant is cationic and said surfactant is from about 0.12 to about 0.2 percent active.

20. The process of claim 19, wherein $R_3$ and $R_4$ are methyl, or $R_3$ is methyl, and $R_4$ is ethyl, and said aminonitrile metal carboxylate:aminonitrile ratio is from about 0.9–1.1:1 and said equivalent weight ratio of the sum of the aminonitrile metal carboxylate and aminonitrile: $M_1(OCl)_x$ is from about 1:1.2–1.5, and wherein said ammonia source is gaseous ammonia or concentrated ammonium hydroxide.

21. The process of claim 20, wherein said reducing agent is sodium bisulfite or sodium sulfite.

22. The process of claim 21, wherein M is sodium.

23. The process of claim 22, wherein the azonitrile metal carboxylate is neutralized with a mineral acid of HCL.

* * * * *